United States Patent
Wanichwecharungruang et al.

(10) Patent No.: US 12,171,969 B2
(45) Date of Patent: Dec. 24, 2024

(54) DISSOLVABLE MICRONEEDLE

(71) Applicant: Mineed Technology Company Limited, Samut Prakan (TH)

(72) Inventors: Supason Wanichwecharungruang, Bangkok (TH); Teeranut Rutwaree, Rayong (TH); Titiporn Sansureerungsikul, Bangkok (TH); Pravit Asawanonda, Bangkok (TH); Wijit Banlunara, Bangkok (TH)

(73) Assignee: Mineed Technology Company Limited, Samut Prakan (TH)

( * ) Notice: Subject to any disclaimer, the term of this patent is extended or adjusted under 35 U.S.C. 154(b) by 397 days.

(21) Appl. No.: 17/625,813

(22) PCT Filed: Aug. 20, 2019

(86) PCT No.: PCT/TH2019/000031
§ 371 (c)(1),
(2) Date: Jan. 10, 2022

(87) PCT Pub. No.: WO2021/006823
PCT Pub. Date: Jan. 14, 2021

(65) Prior Publication Data
US 2022/0249820 A1    Aug. 11, 2022

(30) Foreign Application Priority Data
Jul. 10, 2019 (TH) .............................. 1901004256

(51) Int. Cl.
*A61M 37/00* (2006.01)
*A61B 17/20* (2006.01)

(52) U.S. Cl.
CPC ....... *A61M 37/0015* (2013.01); *A61B 17/205* (2013.01); *A61M 2037/0046* (2013.01);
(Continued)

(58) Field of Classification Search
CPC ...... A61M 37/0015; A61M 2037/0046; A61M 2037/0061; A61M 2202/30;
(Continued)

(56) References Cited

U.S. PATENT DOCUMENTS

| | | | |
|---|---|---|---|
| 9,993,423 B2 | 6/2018 | Quan et al. | |
| 2005/0118388 A1* | 6/2005 | Kingsford | A61M 37/0015 604/173 |

(Continued)

FOREIGN PATENT DOCUMENTS

| | | |
|---|---|---|
| EP | 3006078 A1 | 4/2016 |
| WO | 2015183179 A1 | 12/2015 |

(Continued)

OTHER PUBLICATIONS

Stearns, Andrea, "Cross-Linked Hyaluronic Acid Injections", blog post dated Mar. 26, 2018, available online at https://www.maylips.com/blog/cross-linked-hyaluronic-acid-injections.html (accessed Apr. 4, 2024). (Year: 2018).*
International Search Report and Written Opinion for PCT/TH2019/000031 dated May 8, 2020.
Examination Report No. 1 issued with corresponding Australian Patent Application No. 2019456606 dated Aug. 3, 2022.
Examination Report No. 2 issued with corresponding Australian Patent Application No. 2019456606 dated Oct. 12, 2022.

*Primary Examiner* — Amber R Stiles
(74) *Attorney, Agent, or Firm* — TROUTMAN PEPPER HAMILTON SANDERS LLP

(57) ABSTRACT

The present invention relates to a dissolvable microneedle comprising needles made of a water-soluble material assembled on one side of a base, which is a sheet material having liquid-permeable cavities, wherein the needles being assembled to the base such that bottom portion of the needles is directly connected to the base, the connection of the bottom portion of the needle s to the base forming through a structure in which the bottom portion of the needles penetrates into the base (102), occupying some or all cavities of the base. The dissolvable microneedle with the structure according to the present invention is convenient to (Continued)

use as the penetrating structure that connects the needle s to the base can be dissolved quickly and efficiently; therefore, the base can be removed from the top skin without the needles embedded within the skin being pulled out. Hence, there is no clearly visible remainder on the top skin, and the active agent contained in or coated on the needles can also be released more effectively.

21 Claims, 8 Drawing Sheets

(52) U.S. Cl.
CPC . *A61M 2037/0061* (2013.01); *A61M 2202/30* (2013.01); *A61M 2207/00* (2013.01)

(58) Field of Classification Search
CPC ...... A61M 2207/00; A61M 2037/0023; A61M 2205/0244; A61M 2037/0053; A61B 17/205; A61K 9/0021
See application file for complete search history.

(56) References Cited

U.S. PATENT DOCUMENTS

| | | | |
|---|---|---|---|
| 2011/0112502 A1* | 5/2011 | Kirby | A61B 17/205 604/500 |
| 2015/0328443 A1* | 11/2015 | Jung | A61K 9/08 427/2.21 |
| 2017/0189660 A1* | 7/2017 | Baek | B05D 1/00 |
| 2017/0189661 A1* | 7/2017 | Lee | A61M 37/0015 |
| 2018/0078498 A1 | 3/2018 | Petersson et al. | |
| 2018/0161252 A1 | 6/2018 | Francis et al. | |

FOREIGN PATENT DOCUMENTS

| | | |
|---|---|---|
| WO | 2019075275 A1 | 4/2019 |
| WO | 2019094349 A1 | 5/2019 |

* cited by examiner

DISSOLVABLE MICRONEEDLE

This application is a United States national stage entry under 35 U.S.C. § 371 of International Application No. PCT/TH2019/000031, filed on Aug. 20, 2019, which claims priority from Thailand patent application Ser. No. 1901004256, filed on Jul. 10, 2019. The entire contents of each application are hereby incorporated by reference in their entirety.

TECHNICAL FIELD

Engineering related to a medical device and medical device design, particularly to a dissolvable microneedle

BACKGROUND OF THE INVENTION

A microneedle can solve the problem of delivering medicament transdermally since it can penetrate the stratum corneum, therefore enabling the medicament to be delivered into the skin. Generally, the microneedle length can be determined as desired, for example, the needle length of a microneedle that is not so long that it reaches the nervous system will not cause pain, the needle length that does not reach the blood vessel allows bloodless application, the microneedle made of a material that dissolves in the tissue and is non-biotoxic provides a microneedle that can dissolve in the tissue, which is generally referred to as a "dissolvable microneedle". The microneedle is usually produced in a form of an array with numerous needles on the same array. By "microneedle", sometimes it can encompass a structure containing both the needles and needle array. When an active agent is put into the dissolvable needles, the active agent can then be delivered into the skin concurrently with the needles.

One of the major problems in the art of dissolvable microneedle is that the microneedle must be applied with the base of the needle array which can be seen easily remaining on the skin for a long time. This is because the bottom portion of the needles that is connected to the base being on the skin cannot detach from the base immediately, the base must therefore remain attached to the skin such that it can be clearly seen on the skin for a sufficiently long time for the needles embedded in the skin to dissolve. This causes inconvenience as the base must remain attached to the skin for a long time. In case where the base is removed before the bottom portion of the needles completely detaches from the base or completely dissolves, some part of the needle will be removed together with the base, therefore compromising the efficiency of the active agent delivery of the microneedle.

There are attempts to improve the structure and characteristics of the microneedle to obtain a better performance. Examples of the prior art are as follows.

U.S. Pat. No. 9,993,423 discloses a microneedle that contains a drug only at the tip portion of the needles. The needle tip portion of the dissolvable microneedle is immersed in a solution containing a drug and highly concentrated water-soluble polymer.

US patent publication no. US 2018/0078498 discloses a microneedle wherein the needles of the microneedle consist of two separate layers of polymers. The needle tip portion consists of a drug and a polymer which can provide a sustained drug release for at least two days after the needles are embedded in the skin. The bottom portion of the needles consists of a fast-dissolving polymer. Therefore, upon applying the microneedle to the skin, the bottom portion of the needles will dissolve, allowing the needle tip portion to remain embedded in the skin.

US patent publication no. US 2018/0161252 discloses a microneedle consisting of three layers: the first layer is the needles of the microneedle, the second layer is the base of the microneedle made of a water-soluble polymer, and the third layer is a water-permeable material. This microneedle is used by providing a liquid to the third layer to cause the second layer to dissolve and waiting until the second layer completely dissolves to remove the remaining base of the microneedle.

However, the dissolvable microneedles currently used and mentioned in the above prior arts still have disadvantages in use, i.e. when using the microneedle by embedding the needles in the skin, the bottom portion of the needles is still connected to the base located on the skin and must be remained in such condition for a long time until the needles embedded in the skin completely dissolve. Then, the base can be removed from the skin without the needles being removed. Leaving the base which is still connected to the needles on the skin for a long time causes a negative effect, i.e. making the openings on the skin last longer, therefore posing a risk of infection and requiring skin repair afterward which will cause undesired dark spots on the user's skin.

SUMMARY OF THE INVENTION

The present invention relates to a dissolvable microneedle comprising needles made of a water-soluble material assembled on one side of the base, which is a sheet material having liquid-permeable cavities. The needles are assembled to the base such that the bottom portion of the needles is directly connected to the base. The connection of the bottom portion of the needles to the base forms through a structure in which the bottom portion of the needles penetrates into the base, occupying some or all cavities of the base.

An object of the present invention is to provide a dissolvable microneedle with a structure that is convenient to use as the penetrating structure that connects the needles to the base can dissolve quickly and effectively; therefore, the base can be removed from the skin without the needles embedded within the skin being pulled out. Hence, there is no obvious any remainder on the skin, no openings on the skin after application, and the active agent contained in or coated on the needles can also be released more effectively.

In a further embodiment, the present invention also relates to a dissolvable microneedle having a structure with fewer layers which results in a thinner microneedle that is therefore adaptable to the curvature of the user's skin and can be used over a wide area of skin in a more convenient and effective manner.

In an alternative embodiment, the dissolvable microneedle according to the present invention can also be in a form such that the needles of the microneedle have a hook shape at the tip portion of the needles and/or on the side portion of the needles so that the tissue is hooked after inserting the needles, making it more difficult to pull out the needles from the tissue.

Furthermore, the present invention also involves a dissolvable microneedle having the aforementioned features, wherein the needles contain any active agent and/or any cells such as living cells, a vaccine together with a vaccine adjuvant, vitamin, drug, RNA, DNA, natural extract, peptide, *Botulinum* toxin A, melanocyte, cancer cells, stem cells or a combination thereof, as well as the use of the dissolvable microneedle according to the present invention in a treatment and/or therapy of a disease for the physiological therapy and/or improvement and/or alteration and/or repair, and/or the cosmetic use in human or animals.

DETAILED DESCRIPTION

Figure 1:
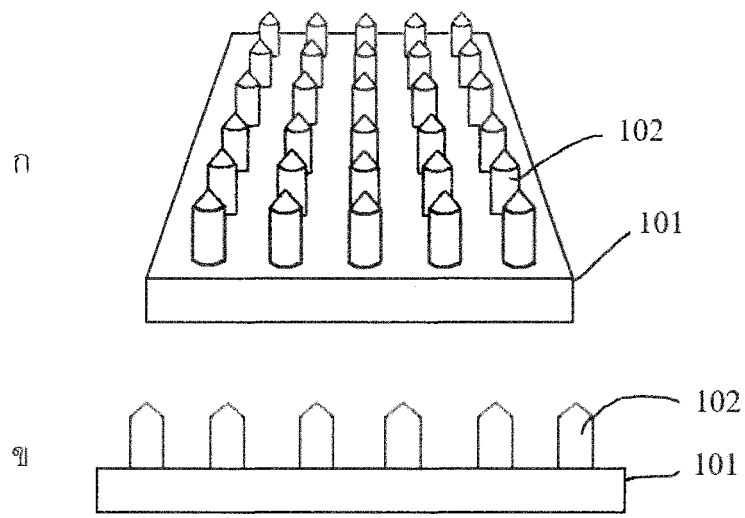
FIG. 1 shows the dissolvable microneedle according to an exemplary embodiment of the present invention, wherein 1a shows a perspective view of the dissolvable microneedle and 1b shows a side view of the dissolvable microneedle.
Figure 2:
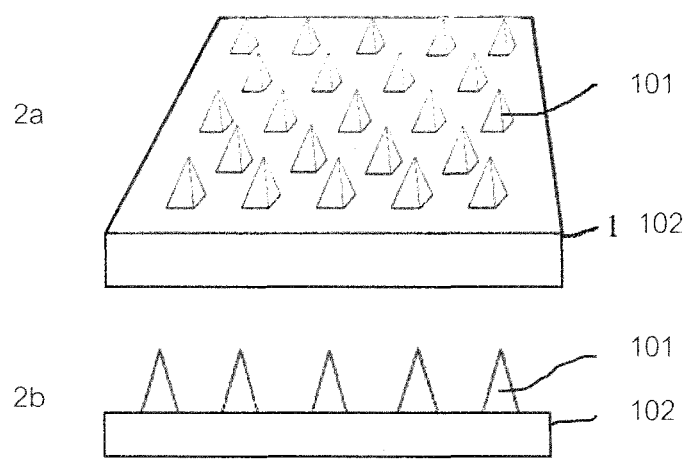
FIG. 2 shows the dissolvable microneedle according to another exemplary embodiment of the present invention, wherein 2a shows a perspective view of the dissolvable microneedle and 2b shows a side view of the dissolvable microneedle.

FIGS. 1 and 2 show the dissolvable microneedle according to an exemplary embodiment of the present invention comprising needles (101) made of a water-soluble material assembled on one side of the base (102), which is a sheet material having liquid-permeable cavities.

According to the present invention, the needles (101) can be made of any water-soluble materials that are non-biotoxic and bio-absorbable and bio-compatible. Examples of appropriate material used to make the needles (101) are cross-linked or non-cross-linked bio-absorbable and bio-compatible polymer, preferably hyaluronic acid, polyvinylpyrrolidone, polyvinyl alcohol, silkworm sericin, collagen, bio-absorbable sugar or a combination thereof. Preferably, the needles (101) are made of a material comprising hyaluronic acid in an amount of 30-60% by weight and further comprising a component selected from polyvinylpyrrolidone, polyvinyl alcohol, silkworm sericin, collagen, maltose, galactose, glucose, sucrose, fructose, xylose, xylitol and a combination thereof which can be selected without limitation by those skilled in the art.

The needles (101) can be in any shape such as shown in FIG. 1 wherein the needles (101) have a pointed cylindrical shape, or as shown in FIG. 2 wherein the needles (101) have a square-based pyramidal shape. However, the shape of the needles (101) of the present invention can be improved or changed so that it is suitable for the application of microneedle.

The distance between each needle (101) aligned on the base (102) can be as desired. For example, the distance between each needle (101) may be in a range from 20 to 10000 microns, preferably in a range from 100 to 500 microns.

The number of the needles (101) on the base (102) can be altered so that it is suitable for the microneedle size and the distance between each needle (101) desired.

The length of the needles (101) can be altered so that it is suitable for the application. For example, the length of the needles (101) may be in a range from 50 to 3,000 microns, preferably in a range of 50 to 1,500 microns.

According to the present invention, the base (102) should preferably be a sheet material having cavities that allow permeation of liquid such as water or ethanol. Said material is non-biotoxic, does not cause skin irritation upon contact, and does not release any biotoxic chemical or fiber upon receiving water or appropriate liquids. Examples of appropriate sheet material for using as a base (102) according to the present invention are woven patch, non-woven patch, polymer patch having liquid-permeable cavities, synthetic fabric patch, natural fabric patch, different kinds of paper such as those made of fibers that does not contain a biotoxic filler or binder, and a combination thereof which can be selected without limitation by those skilled in the art.

For example, the woven patch is a synthetic fabric patch or natural fabric patch, the non-woven patch is paper, and the polymer patch having liquid-permeable cavities is an open-cell-sponge patch or porous hydrophilic polymer patch.

The base (102) can have different thicknesses depending on the application or design of the microneedle in various embodiments of the invention. For example, the base (102) may have a thickness in a range from 5 to 10,000 microns, preferable from 100 to 5,000 microns, more preferably from 100 to 3,000 microns.

Figure 3:
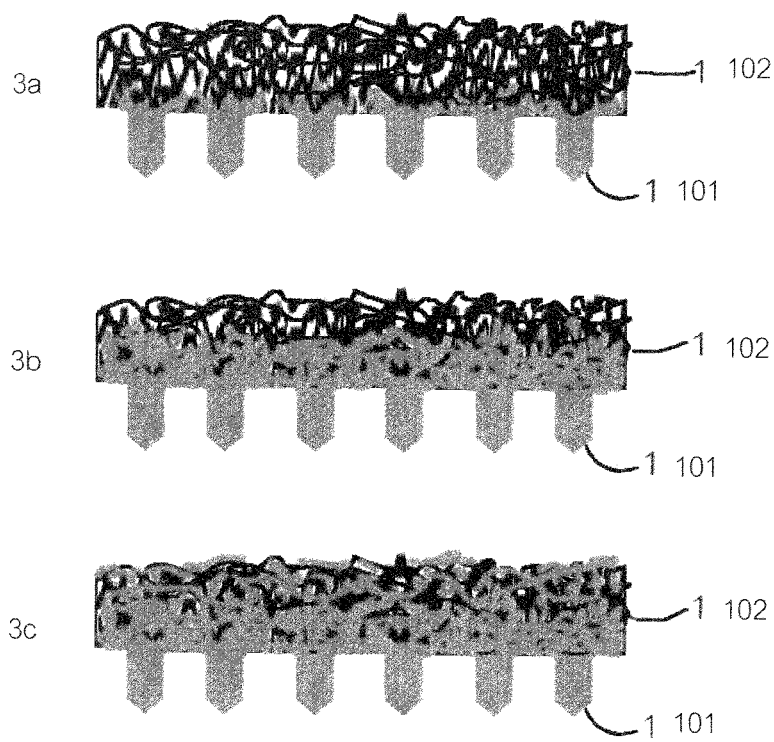
FIG. 3 shows a structure which is a connection of the needles and the base of the dissolvable microneedle according to an exemplary embodiment of the present invention, wherein 3a shows a connection of the needles and the base forming through a structure which is a low-level penetration of the bottom portion of the needles into the cavities of the base; 3b shows a connection of the needles and the base forming through a structure which is an intermediate-level penetration of the bottom portion of the needles into the cavities of the base; and 3c shows a connection of the needles and the base forming through a structure which is a penetration of the bottom portion of the needles into the cavities of the base, wherein the bottom portion of the needles penetrates the cavities of the base until it reaches the other side of the base where the needles are assembled.
Figure 6:
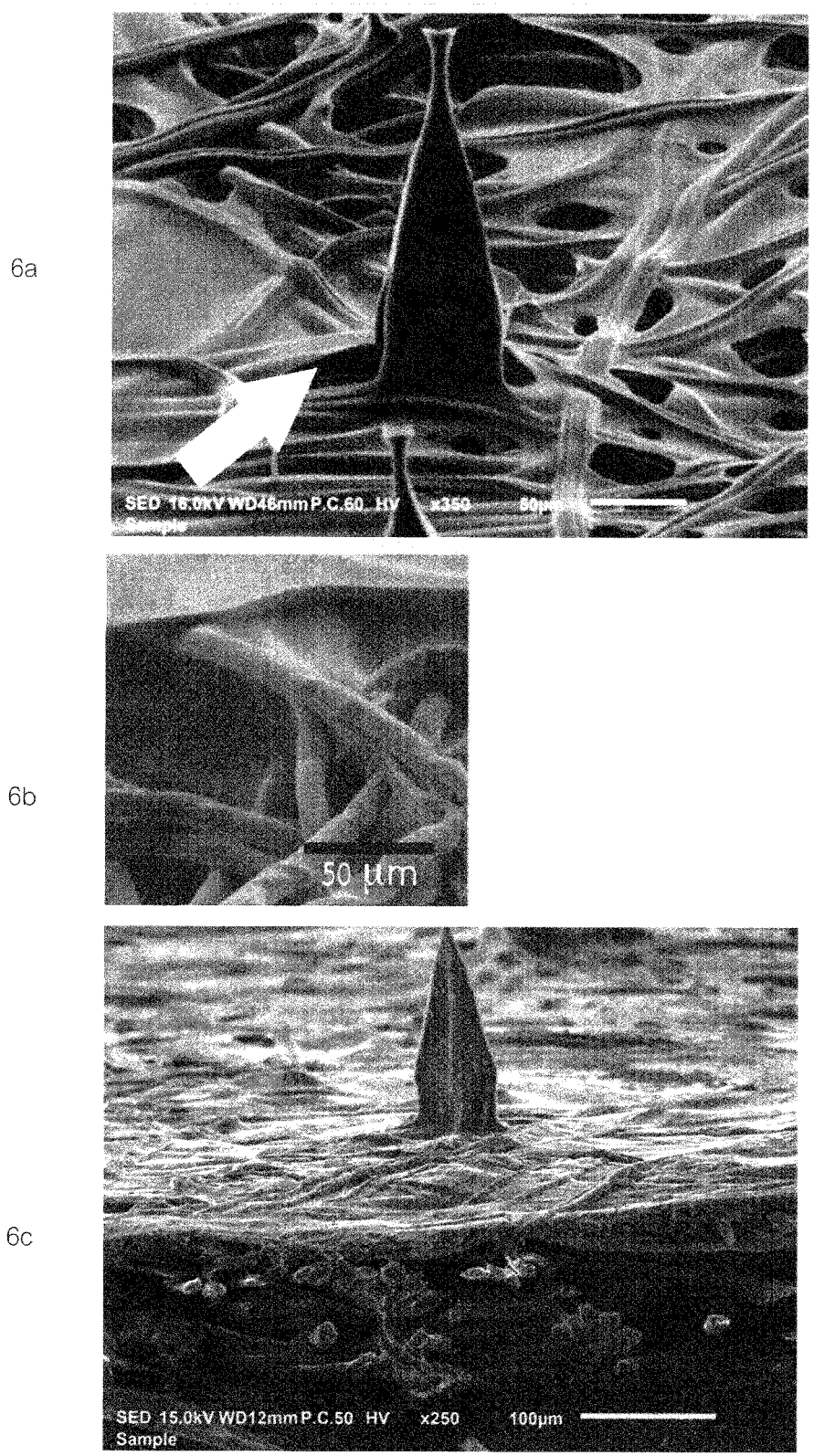
FIG. 6 is an image obtained from a scanning electron microscope at 350× magnification for FIGS. 6a and 6b and 250× magnification for FIG. 6c showing some parts of the dissolvable microneedle's structure according to an exemplary embodiment of the present invention, wherein 6a shows an appearance of the bottom portion of the needles connected to the base, 6b shows an enlarged view of the structure which penetrates into the base, which is the region indicated by an arrow in FIGS. 6a, and 6c shows a cross-sectional side view of the base which reveals the polymer structure connected to the bottom portion of the needles which penetrates the base, which is an entangled fibrous patch having cavities.
Figure 7:
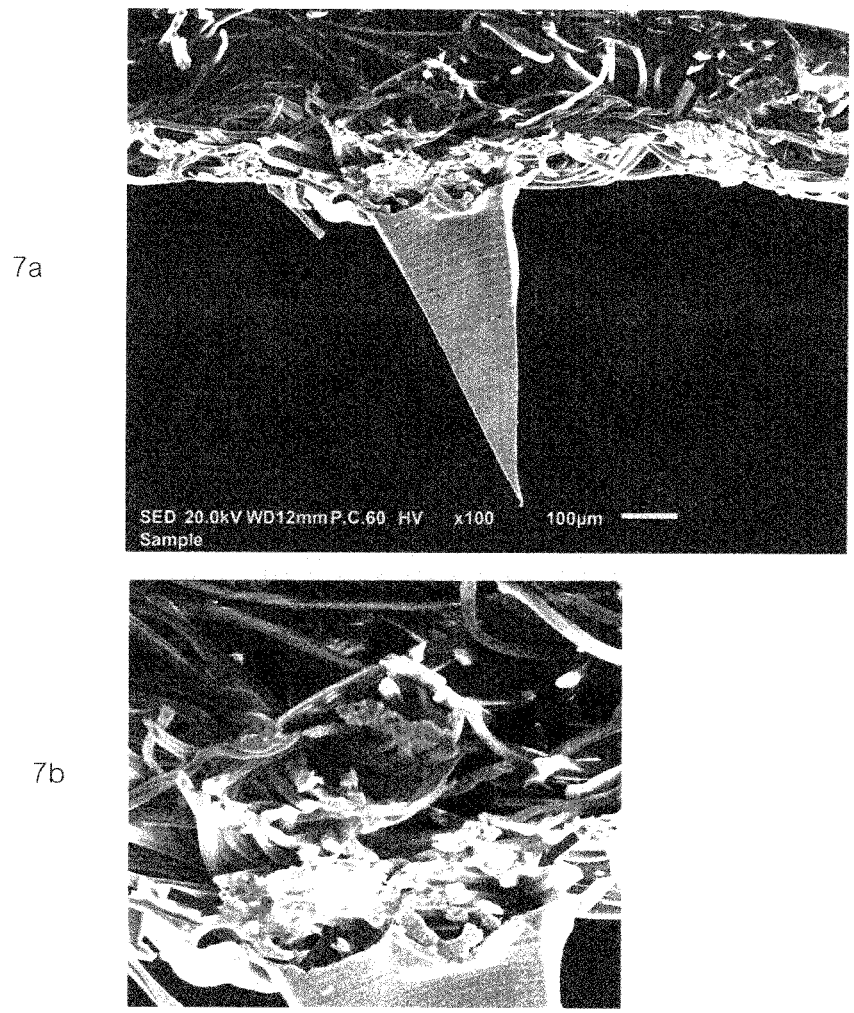
FIG. 7 is an image obtained from a scanning electron microscope at 100× magnification showing a side view of some parts of the structure of the dissolvable microneedle's needles and base according to an exemplary embodiment of the present invention, wherein 7a shows an appearance of the bottom portion of the needles that is connected to the base, and 7b shows an enlarged view of FIG. 7a in the region of the bottom portion of the needles having the polymer structure that penetrates the base, which is entangled fibers.

As shown in FIGS. 3, 6 and 7, the assembling of the needles (101) to the base (102) according to the present invention is such that the bottom portion of the needles (101) is directly connected to the base (102). The connection of the bottom portion of the needles (101) to the base (102) occurs through a structure which is a penetration of the bottom portion of the needles (101) into the base (102), wherein such penetrating structure occupies some or all cavities of the base (102).

The penetration of the bottom portion of the needles (101) into the base (102) according to the present invention can occur in various manners such as in a manner that the bottom portion of the needles (101) penetrates all cavities in the surface region of the base (102) on the side where the needles (101) is assembled with only partial penetration into the cavities inside the base (102), in a manner that the bottom portion of the needles (101) penetrates into some cavities in the surface region of the base (102) on the side where the needles (101) is assembled with only partial penetration into the cavities inside the base (102), or in a manner that the bottom portion of the needles (101) penetrates into all cavities of the base (102), both the cavities in the surface region of the base (102) on the side where the needles (101) is assembled and the cavities inside the base (102). FIGS. 3a-3c show the penetrations of the bottom portion of the needles (101) into the cavities of the base (102) at low and intermediate levels and into the cavities of the base (102) until it reaches the other side of the base (102) where the needles (101) is located, respectively.

In detail, the manner of assembling the needles (101) to the base (102) according to the present invention is a connection of the bottom portion of the needles (101) in a penetrating manner into the base (102), with a material that connects the bottom portion of the needles (101) to the base (102) occupying all or some cavities of the base (102). The penetration of the bottom portion of the needles (101) into the cavities of the base (102) can be such that a material connected to the bottom portion of the needles (101) occupies the cavities of the surface region of the base (102) on the side where the bottom portion of the needles (101) is located and slightly penetrates into the base (102) (as shown in FIG. 3a). However, there could be a greater level of penetration, i.e. the connection of the bottom portion of the needles (101) is a penetration from the side where the needles (101) is located into both the cavities in the surface region on the side where the needles (101) are located and the some cavities inside the base (102), but the penetration does not completely fill the cavities of the base (102) (as shown in FIG. 3b and exemplified in FIG. 7). The penetration could be at a high level, i.e. the connection of the bottom portion of the needles (101) that penetrates the cavities inside the base (102) and pierces through the other side of the base (102) (as shown in FIG. 3c). The connection of the bottom portion of the needles (101) which is a penetration into the base (102) can be in any manner above, depending on many factors such as the thickness of the sheet material used to make the base (102) and the type of the material used to make the needles (101). Moreover, the process of making the microneedle can also affect the structure that connects the bottom portion of the needles (101) to the base (102).

The bottom portion of the needles (101) penetrating the base (102) can be made of any water-soluble materials that are non-biotoxic and bio-absorbable and bio-compatible and can be selected from the materials used to make the needles (101) mentioned above.

The direct attachment of the needles (101) to the base (102) such that the connection of the bottom portion of the needles (101) penetrates the base (102) according to the present invention is a characteristic that has a significantly advantageous effect on the detachment speed of the needles (101) from the base (102). Therefore, the microneedle according to the present invention can be used in a convenient and highly effective manner.

The needles (101) can contain any non-specific active agent so that the microneedle according to the invention can be used in a treatment and/or therapy of a disease for the physiological therapy and/or improvement and/or alteration and/or repair, and/or the cosmetic use in human or animals. The active agent contained in the needles (101) can be such that it is homogeneously dissolved into the material used to make the needles (101) or not homogeneously dissolved into the material used to make the needles (101). The active agent can be dispersed throughout the needles (101) or accumulate in a certain region such as the tip portion of the needles (101). The active agent can be in a form of the sole active agent without encapsulation or formed as any compounds with other additives, or the active agent may be encapsulated in any carrier, i.e. the active agent can be encapsulated in a particle of any material. The active agent may be in a form of a complex compound with cyclodextrin or materials stored in liposome, or an encapsulation. The active agent may be in a form of small particles of the active agent itself. The active agent could be a drug, supplement or any bioactive agent. Examples of active agent are vitamin C and/or any derivatives thereof and/or vitamin A and/or any derivatives thereof and/or minoxidil and/or *Botulinum* toxin A and/or glutathione and/or triamcinolone and/or any anesthetic and/or anti-inflammatory drug and/or any antibiotic, RNA, DNA, natural extract, peptide or a combination thereof. However, the examples of active agent mentioned herein are only intended to facilitate understanding of the present invention and not intended to limit the present invention.

The needles (101) may contain any cells. Examples of cell contained in the needles are melanocyte, stem cell, leucocyte, keratinocyte, fibroblast, different types of cancer cell, any pathogen causing weakness, any dead pathogen, any living pathogen. The cells in the needles (101) can be contained together with or without a cell medium.

In an exemplary embodiment, the needles (101) may contain living cells in an amount of 100 to 1,000,000 cells per square centimeter of the needle array, *Botulinum* toxin A in an amount of 1 unit to 50,000 units per square centimeter of the needle array, melanocyte in an amount of 10 to 1,000,000 cells per square centimeter of the needle array, cancer cell in an amount of 10 to 1,000,000 cells per square centimeter of the needle array, or stem cell in an amount of 10 to 1,000,000 cells per square centimeter of the needle array, etc. According to the present invention, the term "needle array" means all areas with the needles-assembled region, as well as the region without the needles, i.e. all areas of the patch applied to the skin.

In an advantageously alternative embodiment, the present invention also involves a microneedle characterized in that the needles (101) of the microneedle have a hook shape at the tip portion of the needles (101) and/or on the side portion of the needles (101) so that the tissue is hooked after inserting the needles (101), making it more difficult to pull out the needles (101) from the tissue. The feature of the needles described herein can be used in conjunction with the aforementioned-features of the microneedle. The hook may be a curved or angled hook. The hook can be located on the lateral side or can be in any number. This hook embodiment should encompass needles with barbs or protrusions protruding from the surface of the needles (101) which generally makes the withdrawal of the needles (101) more difficult.

The dissolvable microneedle according to the present invention can be used in various manners depending on user's convenience. For example, upon applying the microneedle and pressing the needles (101) so that they penetrate the skin, one can apply a cotton soaked with saline or purified water or any suitable liquid to the base (102) located on the skin and hold it for a moment to allow the bottom portion of the needles (101) to dissolve. Then, the base (102) can be removed from the skin while the needles (101) remains embedded in the skin. Pressing the cotton soaked with liquid against the base (102) is only an example of the application. The user can wet the base (102) by using any convenient means such as spraying with water or dripping water onto said base (102). The method of wetting the base (102) can be performed in non-limiting, various manners.

Figure 4:
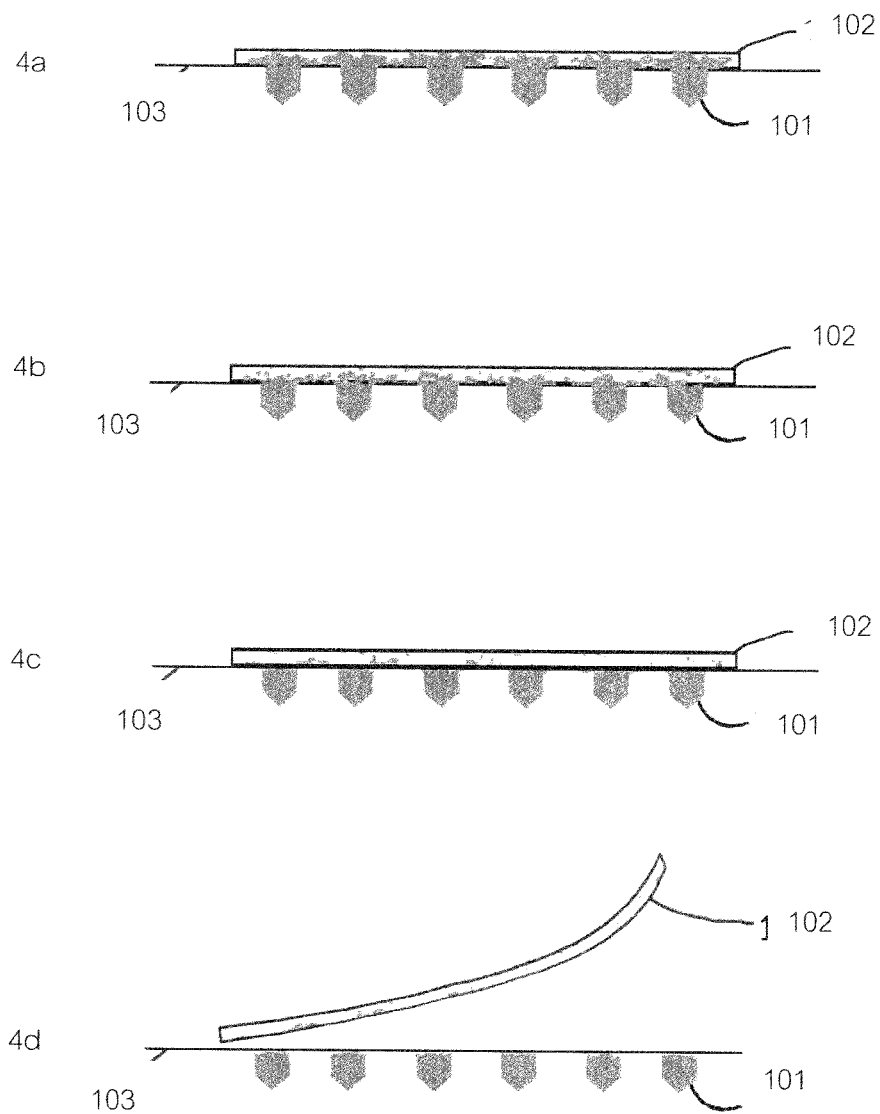
FIG. 4 shows the appearances of the dissolvable microneedle according to an exemplary embodiment of the present invention in an application, wherein 4a shows an appearance of the microneedle when starting to apply to the user's skin; 4b shows an appearance of the microneedle when starting to provide water to the base; 4c shows an appearance of the microneedle after being provided with water for a period of time until the structure which is a penetration of the bottom portion of the needles into the cavities of the base dissolve; and 4d shows an appearance of the microneedle when the structure which is a penetration of the bottom portion of the needles into the cavities of the base almost dissolve completely and the base is subsequently removed from the user's skin.
Figure 5:
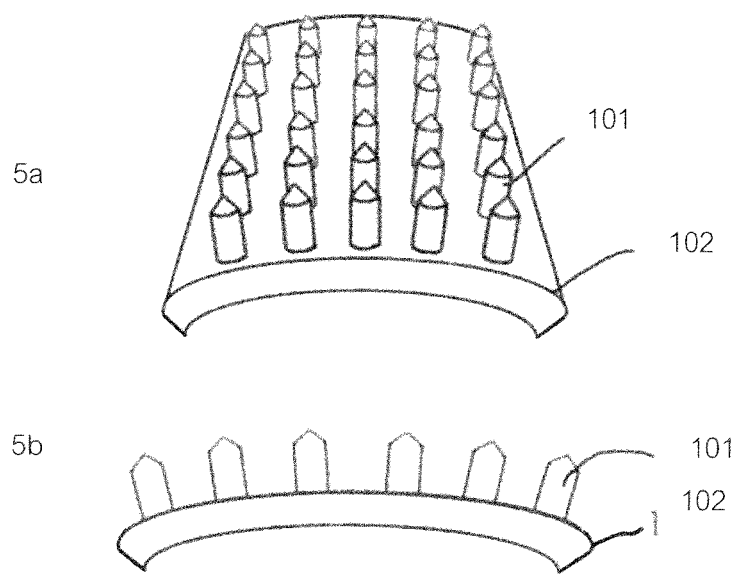
FIG. 5 shows an appearance of the dissolvable microneedle according to an exemplary embodiment of the present invention which is flexible, wherein 5a shows a perspective view of the dissolvable microneedle and 5b shows a side view of the dissolvable microneedle.

FIG. 4 shows an aspect of when using the microneedle according to the present invention by applying the needle (101) side of the microneedle to the skin (103) and pressing the needles (101) so that they embed in the skin (103) and subsequently providing water or suitable liquid to the base (102) located on the skin (103). After the water or liquid was absorbed into the base (102), the structure which attaches the needles (101) to the base (102) and penetrates the cavities of the base (102) will be provided with water or liquid and therefore dissolves. After this connecting structure dissolved, the needles (101) are no longer attached to the base (102). The base (102) on the skin (103) therefore can be removed without the needles (101) embedded in the skin (103) being withdrawn. Hence, there is no visible patch left on the skin (103) in the application.

According to the present invention, the penetrating structure which connects the needles (101) to the base (102) and is located inside the base (102) rapidly and effectively dissolves due to the liquid retaining property of the base (102) that allows the base (102) to be removed from the skin (103) in a short period of time without the needles (101) embedded in the skin (103) being withdrawn but remaining embedded in the skin (103). The active agent or cells therefore can be released effectively.

Besides allowing the needles (101) to detach from the base (102) in a short period of time, the direct connection of the needles (101) to the base (102) according to the present invention also reduces the spillage of water or liquid when using the microneedle, i.e. when providing water to the base (102) which has water or liquid-permeable cavities, the water or liquid will destroy the penetrating structure that directly connects the needles (101) to the base (102) since such structure is located in the liquid receiving cavities of the base (102). The base (102) therefore acts as a container that retains water or liquid in the region where such penetrating structure is located. Particularly, choosing the base (102) that is made of a hydrophilic material, i.e. a material capable of absorbing water quickly, will cause this connecting, penetrating structure to be destroyed by water more quickly. The ability to retain water in the cavities of the base (102) also helps to retain the solution generated from the dissolving connecting structure, therefore reducing the spillage when using the microneedle.

The microneedle according to the present invention can be used more conveniently than those of the prior arts, i.e. by applying the microneedle according to the present invention to the skin (103) with the needles (101) embedded in the skin (103) and the base (102) above the skin (103), then providing water or suitable liquid to the base (102) to allow removal of the base (102) without the needles (101) being withdrawn or spending a lot of time.

In an exemplary embodiment of the present invention, the time required for the microneedle to be pressed against the skin (103) after providing the base (102) with water or suitable liquid can be in range from 1 second to 3 minutes or longer. Preferably, the length of time can be varied depending on the type of material that is the structure attaching the needles (101) to the base (102). Generally, it can be the same material as that used to make the needles (101) or a different material. Preferably, it should be a material that dissolves well in water. Examples of suitable material are the materials used to make the needles (101), fast-dissolving polymer which can be the same with that used to make the needles (101). If such material can dissolve quickly in water, the base (102) can be removed within 3 to 30 seconds which is very convenient for the user, and allows the opening pores on the skin to close in a short time.

Another advantage of the present invention is that the microneedle can be flexible if the material used to make the base (102) is a flexible sheet material. Moreover, the characteristics of the microneedle having the needles (101) assembled directly on the base (102) according to the present invention enables a production of large microneedle whose needle array is adaptable to the skin curvature.

Experiment

An experiment was conducted by comparing the application of different microneedles:
1) a commercially available conventional microneedle having needles and base that are made of the same material, hereinafter referred to as "Microneedle a)",
2) a comparative microneedle having a base that is connected as a single material to the needles, which is connected to a water-permeable-material sheet via a connecting material layer or polymer layer that attaches the microneedle array to the water-permeable-material sheet, hereinafter referred to as "Microneedle b)", and
3) a microneedle according to the present invention having needles (101) assembled on the base (102), which is made of a sheet material having water-permeable cavities, hereinafter referred to as "Microneedle c)".

The needle array tested has a dimension of 1×3 cm$^2$. The characteristics of the needle array are as follows:
the distance between the needles is 500 microns,
the number of needles/cm$^2$ is 441 needles/cm$^2$,
the needles are made of a polymer mixture of hyaluronic acid and sucrose in the ratio of 50:50 by weight,
the needles have a square-based pyramidal shape with 100×100 square microns pyramid base,
the needles are 300-microns tall,
the Microneedle a) has a 1,000-microns thick base, the Microneedle b) has a 300-microns thick base made of the same material as the needle and a 100-microns thick polymer layer that connects the base to a 300-microns thick water-permeable sheet material, which is a fabric free of pills and fluorescent woven from synthetic fibers of polyester/wood pulp, the Microneedle c) has a 300-microns thick fabric base free of pills and fluorescent and woven from synthetic fibers of polyester/wood pulp.

All three microneedles were tested on a piglet's fresh hairless belly skin. A 3×5 cm² pig skin was placed against the curved surface of a glass beaker having a 3.5-cm radius round base and 5-cm tall lateral side forming the curved lateral surface of the beaker. The lateral edges of the pig skin were attached to the beaker surface using an adhesive tape so that the pig skin is attached to the lateral curved surface of the beaker to simulate the skin that curves along the body. The test results are shown in the below table.

| Tested object | Test results | | |
|---|---|---|---|
| | Microneedle a) | Microneedle b) | Microneedle c) |
| Attachment of a 1 × 3 cm² array | The whole array was able to be attached to the curved pig skin. However, it needed to be pressed all the time, otherwise the needle array would come off. | The whole array was able to be attached to the curved pig skin. However, it needed to be pressed all the time, otherwise the needle array would come off. The adhesive tape was used to attach the needle array on all sides to the pig skin. | The whole array was able to be attached to the curved pig skin easily. After being pressed, the needle array did not come off. |
| Providing water to a 1 × 3 cm² microneedle array placed on the pig skin after attachment | No action required | Providing water by soaking a cotton in water and placing it on the needle array | Providing water by soaking a cotton in water and placing it on the needle array |
| The attachment of the needles to the base upon removing the base after applying for 3 seconds | The attachment of the needles is 100% | The attachment of the needles is 100% | The attachment of the needles is 8 ± 3% without any obvious needle part on the pig skin |
| The attachment of the needles to the base upon removing the base after applying for 5 seconds | The attachment of the whole needle is 93 ± 4%. The rest are the needles with dissolved and broken tip portion whose bottom portion remains clearly visible. | The attachment of the needle is 91 ± 5%. The rest are the needles with dissolved or broken tip portion whose bottom portion remains clearly visible. | There is no needle attached to the base. No needle part remains visible on the pig skin. |
| The attachment of the needles to the base upon removing the base after applying for 60 seconds | The attachment of the whole needle is 90 ± 4%. The rest are the needles with dissolved or broken tip portion whose bottom portion remains clearly visible. | No needle is attached to the base, but the base which is a patch remains clearly visible on the pig skin. | There is no needle attached to the base. No needle part remains visible on the pig skin. |
| The attachment of the needles to the base upon removing the base after applying for 3 minutes | The attachment of the needle is 72 ± 9%. The rest are the needles with dissolved or broken tip portion whose bottom portion remains clearly visible. | No needle is attached to the base, but the base which partially dissolved as a sticky substance remains visible on the pig skin. | There is no needle attached to the base. No needle part remains visible on the pig skin. |

Samples and Test Results for the Application of the Microneedle According to the Present Invention Example 1: A microneedle has a dimension of 1×1 cm². Its needles (101) are made of a mixture of hyaluronic acid and sucrose with the ratio of hyaluronic acid to sucrose at 50:50 by weight. The needles (101) are assembled on the base (102) which is a fabric free of pills and fluorescent and woven from synthetic fibers of polyester/wood pulp. The fabric is approximately 200-microns thick. The needles (101) have a cylindrical shape with a 100×100 square microns of square base. The needle tip portion is pointed in a form of a hook at the tip portion. The needles are 300-microns tall. Each needle is located 500 microns away from each other. The connection of the bottom portion of the needles (101) to the base (102) is a direct connection of the bottom portion of the needles (101), wherein the material of the needles' bottom portion continues to fill some cavities between the fabric fibers, both the cavities on the fabric surface and the cavities in the fabric (as shown in FIG. 6). The microneedle was applied to the skin. A cotton soaked with water was then placed above the microneedle and pressed for 5 seconds before being removed. The base (102) was subsequently removed and examined. No needle (101) was found attached to the base (102).

Example 2: A microneedle has a dimension of 1×1 cm². The needles (101) are made of a mixture of hyaluronic acid and silkworm sericin with the ratio of hyaluronic acid to silkworm sericin at 50:50 by weight. The needles (101) are assembled on the base (102) which is a fabric free of pills and fluorescent and made of polyester/wood pulp. The fabric is approximately 300-microns thick. The needles (101) have a pyramidal shape with a 100×100 square microns of square base and a height of 300 microns. Each needle is located 500 microns away from each other. The connection of the bottom portion of the needles (101) to the base (102) is a direct connection of the bottom portion of the needles that continues to fill the cavities between the fabric fibers, both the cavities on the fabric surface and the cavities in the fabric. The structure connecting the needles (101) to the fabric penetrates the fabric until it pierces through the other side of the fabric. The microneedle was applied to the skin. The base (102) was sprayed with water and pressed for 30 seconds. The base (102) was then removed and examined. No needle (101) was found attached to the base (102).

Example 3: A microneedle has a dimension of 5×5 cm$^2$. The needles (101) are made of a mixture of hyaluronic acid and sucrose with the ratio of hyaluronic acid to sucrose at 60:40 by weight. The needles (101) are assembled on the base (102) which is a fabric free of pills and fluorescent and made of polyester/wood pulp. The fabric is approximately 300-microns thick. The needles (101) have a pyramidal shape with a 100×100 square microns of square base and a height of 300 microns. Each needle is located 500 microns away from each other. The connection of the bottom portion of the needles (101) to the base (102) is a direct connection of the bottom portion of the needles that continues to fill the cavities between the fabric fibers, both the cavities on the fabric surface and the cavities in the fabric. The structure connecting the needles to the fabric penetrates the fabric but does not pierce through the other side of the fabric. The microneedle was applied to the skin. A cotton soaked with water was then placed above the microneedle and pressed for 5 seconds before being removed. The base (102) was subsequently removed and examined. No needle (101) was found attached to the base (102).

Example 4: A circular microneedle has a diameter of 1.5 cm. The needles (101) are made of a mixture of hyaluronic acid and polyvinylpyrrolidone and sucrose with the ratio of hyaluronic acid to polyvinylpyrrolidone to sucrose at 50:30:20 by weight. Each needle array contained retinaldehyde, vitamin C and vitamin E in an amount of 100 μg, 1.5 mg and 2.0 mg, respectively. The needles (101) are assembled on the base (102) which is a fabric free of pills and fluorescent and made of polyester/wood pulp. The fabric is approximately 300-microns thick. The needles have a cylindrical shape with a 100×100 square microns of square base and a height of 300 microns. Each needle is located 500 microns from each other. The pointed tip portion has a hook shape which helps to hook the tissue. The connection of the bottom portion of the needles (101) to the base (102) is a direct connection of the bottom portion of the needles that continues to fill the cavities between the fabric fibers, both the cavities on the fabric surface and the cavities in the fabric. The structure connecting the needles (101) to the fabric penetrates the fabric but does not pierce through the other side of the fabric. The microneedle was applied to the skin. A cotton soaked with water was then placed above the microneedle and pressed for 5 seconds before being removed. The base (102) was subsequently removed and examined. No needle (101) was found attached to the base (102). This microneedle was tested for the wrinkle treatment by applying the needle array to the wrinkles every week for three months. It was found that the wrinkles clearly became shallower.

Figure 8:
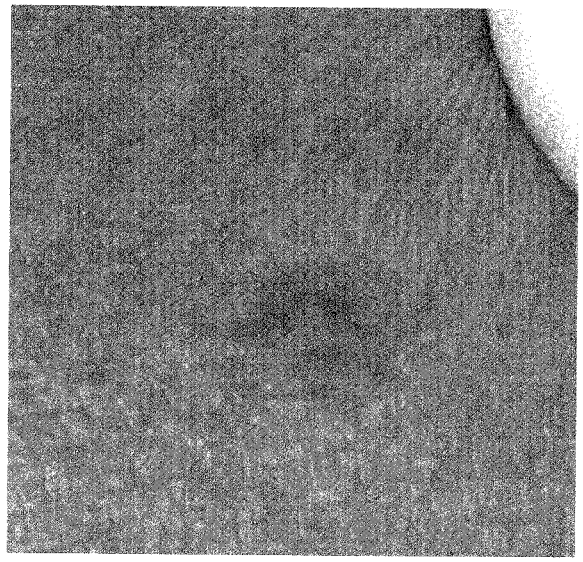
FIG. 8 is an image obtained from VISIA Complexion Analysis System of Canfield Scientific Inc., Parsippany-Troy Hills, NJ, USA showing an appearance of an atrophic scar on the user's skin, wherein 8a shows an appearance of the atrophic scar prior to application of the dissolvable microneedle according to the present invention, and 8b shows an appearance of the atrophic scar after applying the dissolvable microneedle according to the present invention twice a week for a period of three months.
Figure 8:
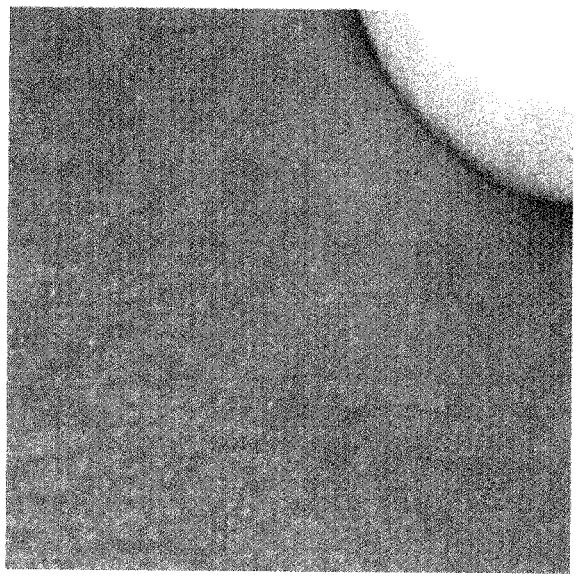

Example 5: A square microneedle has a dimension of 1×1 cm$^2$. The needles (101) are made of a mixture of hyaluronic acid and polyvinylpyrrolidone and maltose with the ratio of hyaluronic acid to polyvinyl-pyrrolidone to maltose at 50:30:20 by weight. Each needle array contained 200-600 nm pro-retinaldehyde particles in an amount equivalent to retinaldehyde of 0.6 mg per square centimeter of the needle array. The pro-retinaldehyde particle is a particle created by retinaldehyde-binding chitosan. The needles (101) are assembled on the base (102) which is a fabric free of pills and fluorescent and made of polyester/wood pulp. The fabric is 200-microns thick. The needles have a pyramidal shape with a 100×100 square microns of square base and a height of 300 microns. Each needle is located 500 microns away from each other. The connection of the bottom portion of the needles (101) to the base (102) is a direct connection of the bottom portion of the needles that continues to fill the cavities between the fabric fibers, both the cavities on the fabric surface and the cavities in the fabric. The penetration of the structure connecting the needles to the fabric is deep into the fabric. The microneedle was applied to the skin in the atrophic scar region. A cotton soaked with water was then placed above the microneedle and pressed for 5 seconds before being removed. The base (102) was subsequently removed and examined. No needle (101) was found attached to the base (102). This microneedle was tested for the atrophic scar treatment by applying the needle array to the atrophic scar region twice a week every week for three months. It was found that the atrophic scar clearly became shallower (as shown in FIG. 8).

Example 6: A microneedle has needles (101) made of a mixture of hyaluronic acid and polyvinylpyrrolidone and maltose with the ratio of hyaluronic acid to polyvinylpyrrolidone to maltose at 60:30:10 by weight. *Botulinum* toxin A (Botox®, supplied by Allergan, Inc., California) was loaded into the needles (101) in an amount of 1-50,000 units per square centimeter of the needle array. The needles (101) have a square-based pyramidal shape with a 300×300 square microns base and a height of 850 microns. Each needle is located 500 microns away from each other. The needles (101) are assembled on the base (102), which is a filter paper. The microneedle was kept at a temperature of 4° C. It was found that all of the microneedles produced could effectively pierce through the pig ear skin whether *Botulinum* toxin A was contained in a small or large amount in such range. The needle array containing *Botulinum* toxin A of 5 units per square centimeter of the microneedle array was applied to the armpits of volunteers having hyperhidrosis, which is abnormally excessive perspiration. It was applied to the armpits by determining the application spot using the iodine starch method to find the most sweating spot at the armpits to be applied with the microneedle containing *Botulinum* toxin A in an area of 2×3 cm$^2$, which requires the application of *Botulinum* toxin A in an amount of 30 units in total. It was found that the volunteers could feel the microneedle being applied but did not feel pain. Upon following up the results of the perspiratory suppression, it was found that there was no perspiration at the armpits for five months. Upon interviewing the volunteers to collect information, it was found that the volunteers scored the pain from the application of the microneedle according to the present invention as lowest pain, which means not painful or zero pain, while scoring the pain from the application of a hypodermic needle to release *Botulinum* toxin A into the armpit skin across the region with high level of perspiration as highest pain, which is 10.

Example 7: A microneedle has needles (101) made of a mixture of hyaluronic acid and polyvinylpyrrolidone and maltose with the ratio of hyaluronic acid to polyvinylpyrrolidone to maltose at 60:30:10 by weight and contained melanocytes in an amount of 100-1,000,000 cells per square centimeter of the needle array. The needles (101) are assembled on the base (102), which is a fabric free of pills and fluorescent and made of synthetic fibers of polyester/wood pulp. The needles (101) have a square-based pyramidal shape with a 100×100 square microns base and a height of 250 microns. Each needle is located 500 microns away from each other. The needle array has a dimension of 1×1 cm². It was kept at a temperature of 4° C. for no more than 72 hours. It was found that every cell amount contained allowed the needles (101) of the microneedle to pierce into the pig ear skin without any problem. Upon applying the needle array containing melanocytes in an amount of 50,000 cells per square centimeter of the needle array to the back of one-month old BALB/cMlac-nu nude mice having a weight in a range of 20-25 g and taking care of the mice in a condition suitable for a BALB/cMlac-nu nude mouse for another 30 days, the melanocytes were clearly found at the junction between the dermis and epidermis in the region where such microneedle was applied.

Example 8: A microneedle has needles (101) made of a mixture of hyaluronic acid and polyvinylpyrrolidone and maltose with the ratio of hyaluronic acid to polyvinylpyrrolidone to maltose at 60:30:10 by weight and contained B16F0 Melanoma cancer cell lines in an amount of 100-1,000,000 cells per square centimeter of the needle array. The needles (101) are assembled on the base (102), which is a fabric free of pills and fluorescent and made of synthetic fibers of polyester/wood pulp. The needles (101) have a square-based pyramidal shape with a 200×200 square microns base and a height of 850 microns. Each needle is located 500 microns away from each other. The needle array has a dimension of 1×1 cm². The microneedle was kept at a temperature of 4° C. for 48 hours. It was found that the needles (101) of the microneedle could pierce into the pig's ear skin without any problem for every cell amount contained. Upon applying the needle array containing such cancer cells in an amount of 50,000-100,000 cells per square centimeter of the needle array to the back of one-month old BALB/cMlac-nu nude mice having a weight in a range of 20-25 g and taking care of the mice in a condition suitable for a BALB/cMlac-nu nude mouse for another 45 days, a cancerous mass was clearly found at the junction between the epidermis and dermis in the region where such microneedle was applied. It was confirmed by a biopsy that the mass found was indeed a cancerous mass whose base was formed under the dermis.

Figure 9:
FIG. 9 is an image obtained from a stereo microscope at 2× magnification showing a pig's ear skin which is embedded with the needles of the dissolvable microneedle according to the present invention.

Example 9: A 1×1 cm² square microneedle has needles (101) made of a mixture of hyaluronic acid and polyvinylpyrrolidone and maltose with the ratio of hyaluronic acid to polyvinyl-pyrrolidone to maltose at 50:30:20 by weight. Each needle array contained 200-600 nm pro-retinaldehyde particles in an amount equivalent to retinaldehyde of 0.8 mg per square centimeter of the needle array. The pro-retinaldehyde particle is a particle created by retinaldehyde-binding chitosan. The needles (101) are assembled on the base (102), which is a fabric free of pills and fluorescent and made of polyester/wood pulp. The needles have a pyramidal shape with a 200×200 square microns of square base and a height of 650 microns. Each needle is located 500 microns away from each other. The connection of the bottom portion of the needles (101) to the base (102) is a direct connection of the bottom portion of the needles that continues to fill the cavities between the fabric fibers, both the cavities on the fabric surface and the cavities in the fabric. The penetration of the structure connecting the needles to the fabric is deep into the fabric. This microneedle was applied to the pig's fresh hairless ear skin. A cotton soaked with water was then placed above the microneedle and pressed for 3 seconds before being removed. The base (102) was subsequently removed and examined. No needle (101) was found attached to the base (102). The pig skin was cut along the needle line and an image of the skin which was cut open so that the inside could be seen was taken, as shown in FIG. 9. The embedment of the needles (101) was found with the pro-retinaldehyde particles shown clearly in yellow. No opening on the skin was observed.

BEST MODE OF THE INVENTION

Best mode of the invention is as described in the detailed description of the invention.

The invention claimed is:

1. A dissolvable microneedle comprising needles made of a water-soluble material assembled on one side of a base, which is a sheet material having liquid-permeable cavities, wherein the needles being assembled to the base such that a bottom portion of each of the needles is directly connected to the base, the connection of the bottom portion of the needles to the base forming a structure in which the bottom portion of the needles penetrates into the base, occupying some or all cavities of the base, wherein the penetrating structure that connects the needles to the base and is located inside the base is configured to dissolve upon wetting the base, allowing the base to be removed from skin while the needles remains embedded in the skin.

2. The dissolvable microneedle according to claim 1, wherein the bottom portion of the needles penetrates into all cavities in a surface region of the base on a side where the needles are assembled, with partial needle penetration into the cavities inside the base.

3. The dissolvable microneedle according to claim 1, wherein the bottom portion of the needles penetrates into some cavities in a surface region of the base, on a side where the needles are assembled, with partial needle penetration into the cavities inside the base.

4. The dissolvable microneedle according to claim 1, wherein the bottom portion of the needles penetrates into all cavities of the base, in both the cavities in a surface region of the base on a side where the needles are assembled and the cavities inside the base.

5. The dissolvable microneedle according to claim 1, wherein the base is made of materials selected from a woven patch, a non-woven patch, a polymer patch having liquid-permeable cavities, a synthetic fabric patch, a natural fabric patch, a paper patch and a combination thereof.

6. The dissolvable microneedle according to claim 5, wherein the woven patch is a synthetic or natural fabric patch, the non-woven patch is a paper patch, and the polymer patch having liquid-permeable cavities is an open-cell-sponge patch or porous hydrophilic polymer patch.

7. The dissolvable microneedle according to claim 1, wherein the base has a thickness ranging from 5 to 10,000 microns.

8. The dissolvable microneedle according to claim 7, wherein a thickness of the base has a range from 100 to 5,000 microns.

9. The dissolvable microneedle according to claim 7, wherein a thickness of the base has a range from 100 to 3,000 microns.

10. The dissolvable microneedle according to claim 1, wherein the needles are made of a cross-linked or non-cross-linked, bio-absorbable, and bio-compatible polymer material.

11. The dissolvable microneedle according to claim 10, wherein the needles are made of a material comprising hyaluronic acid in an amount of 30-60% by weight.

12. The dissolvable microneedle according to claim 10, wherein the cross-linked or non-cross-linked, bio-absorbable, and bio-compatible polymer material is hyaluronic acid, polyvinylpyrrolidone, polyvinyl alcohol, silkworm sericin, collagen, bio-absorbable sugar, or a combination thereof.

13. The dissolvable microneedle according to claim 11, wherein the needles are made of a material further comprising components selected from polyvinylpyrrolidone, polyvinyl alcohol, silkworm sericin, collagen, maltose, galactose, glucose, sucrose, fructose, xylose, xylitol and a combination thereof.

14. The dissolvable microneedle according to claim 1, wherein the needles have a hook shape at a tip portion of the needles and/or on a side portion of the needles.

15. The dissolvable microneedle according to claim 1, wherein the needles contain viable cells in an amount of 10 to 1,000,000 cells per square centimeter of a needle array.

16. The dissolvable microneedle according to claim 1, wherein the needles contain a vaccine together with a vaccine adjuvant.

17. The dissolvable microneedle according to claim 1, wherein the needles contain an active agent that is a vitamin, a drug, an RNA, a DNA, a natural extract, a peptide, or a combination thereof.

18. The dissolvable microneedle according to claim 1, wherein the needles contain *Botulinum* toxin A in an amount of 1 unit to 50,000 units per square centimeter of a needle array.

19. The dissolvable microneedle according to claim 1, wherein the needles contain melanocytes in an amount of 100 to 1,000,000 cells per square centimeter of a needle array.

20. The dissolvable microneedle according to claim 1, wherein the needles contain cancer cells in an amount of 100 to 1,000,000 cells per square centimeter of a needle array.

21. The dissolvable microneedle according to claim 1, wherein the needles contain stem cells in an amount of 100 to 1,000,000 cells per square centimeter of a needle array.

* * * * *